United States Patent
Windolf

(10) Patent No.: US 10,194,802 B2
(45) Date of Patent: Feb. 5, 2019

(54) DEVICE FOR PROCESSING AND TRANSMITTING MEASURED SIGNALS FOR MONITORING AND/OR CONTROLLING MEDICAL IMPLANTS, DIAGNOSTIC DEVICES OR BIOLOGICAL PROCESSES

(75) Inventor: Markus Windolf, Davos (CH)

(73) Assignee: AO Technology AG, Chur (CH)

( * ) Notice: Subject to any disclaimer, the term of this patent is extended or adjusted under 35 U.S.C. 154(b) by 937 days.

(21) Appl. No.: 13/377,476

(22) PCT Filed: Jun. 11, 2009

(86) PCT No.: PCT/CH2009/000198
§ 371 (c)(1),
(2), (4) Date: Jan. 25, 2012

(87) PCT Pub. No.: WO2010/142045
PCT Pub. Date: Dec. 16, 2010

(65) Prior Publication Data
US 2012/0123221 A1    May 17, 2012

(51) Int. Cl.
*A61B 5/00* (2006.01)
*G06F 19/00* (2018.01)

(52) U.S. Cl.
CPC .......... *A61B 5/0031* (2013.01); *A61B 5/4504* (2013.01); *G06F 19/3418* (2013.01)

(58) Field of Classification Search
CPC .. A61B 5/0031; A61B 5/4504; G06F 19/3418
See application file for complete search history.

(56) References Cited

U.S. PATENT DOCUMENTS

| 4,141,349 A | * | 2/1979 | Ory | A61B 5/4504 600/302 |
| 5,542,430 A | * | 8/1996 | Farrugia | A61B 5/0464 128/924 |

(Continued)

FOREIGN PATENT DOCUMENTS

| JP | 2008-534140 A | 8/2008 |
| WO | 2006/105098 A2 | 10/2006 |

(Continued)

OTHER PUBLICATIONS

International Preliminary Report on Patentability dated Dec. 28, 2011 in corresponding International Application No. PCT/CH2009/000198.

*Primary Examiner* — John R Downey
*Assistant Examiner* — Shirley Jian
(74) *Attorney, Agent, or Firm* — Rankin, Hill & Clark LLP

(57) ABSTRACT

Disclosed is a device (1) for processing and transmitting measured signals which correspond to implant parameters or biological parameters for monitoring and/or controlling medical implants, diagnostic devices or biological processes comprising: A) a biocompatible sterilizable covering (9); B) an electronic signal processing device (2) arranged in said covering (9) and electrically connectable to at least one sensor (5) allowing to process measured signals received from said at least one sensor (5); C) a data memory (16) arranged in said covering (9) and electrically connected to said signal processing device (2) allowing to store data received from said signal processing device (2); and D) a data transmission device (4) arranged in said covering (9) and electrically connected to said data memory (16) for transmitting data received from said data memory (16) to a remote data receiving device (6) which is connectable to an external data processing device (8), wherein E) said signal (Continued)

processing device (2) is programmed to calculate statistically relevant data obtained from the said measured signals to reduce the stored data. Disclosed are furthermore methods to monitor or control bone healing or bone distraction implants.

5 Claims, 1 Drawing Sheet

(56) References Cited

U.S. PATENT DOCUMENTS

| | | | |
|---|---|---|---|
| 5,626,579 A * | 5/1997 | Muschler | A61B 17/7216 606/60 |
| 7,097,662 B2 | 8/2006 | Evans, III et al. | |
| 7,187,968 B2 * | 3/2007 | Wolf | A61N 1/08 600/544 |
| 7,429,920 B2 * | 9/2008 | Smythe | A61B 5/0031 340/539.12 |
| 7,682,313 B2 * | 3/2010 | Bodecker et al. | 600/486 |
| 7,686,768 B2 * | 3/2010 | Bodecker et al. | 600/486 |
| 7,787,946 B2 * | 8/2010 | Stahmann et al. | 607/3 |
| 7,931,597 B2 * | 4/2011 | Bodecker et al. | 600/486 |
| 7,931,598 B2 * | 4/2011 | Bodecker et al. | 600/486 |
| 8,002,553 B2 * | 8/2011 | Hatlestad et al. | 434/262 |
| 8,376,953 B2 * | 2/2013 | Bodecker et al. | 600/486 |
| 8,382,677 B2 * | 2/2013 | Bodecker et al. | 600/486 |
| 8,535,222 B2 * | 9/2013 | Ni et al. | 600/300 |
| 8,784,364 B2 * | 7/2014 | Kamen | A61M 5/14224 604/65 |
| 8,915,741 B2 * | 12/2014 | Hatlestad et al. | 434/262 |
| 8,956,295 B2 * | 2/2015 | Ni et al. | 600/301 |
| 9,421,005 B2 * | 8/2016 | Bonutti | A61B 17/0401 |
| 9,610,073 B2 * | 4/2017 | Bonutti | A61B 17/0401 |
| 2005/0085864 A1 | 4/2005 | Schulman et al. | |
| 2005/0090756 A1 * | 4/2005 | Wolf | A61N 1/08 600/546 |
| 2005/0102026 A1 | 5/2005 | Turner et al. | |
| 2005/0113647 A1 | 5/2005 | Lee et al. | |
| 2007/0018810 A1 * | 1/2007 | Smythe | A61B 5/0031 340/539.12 |
| 2008/0039845 A1 * | 2/2008 | Bonutti | A61B 17/0401 606/62 |
| 2010/0185142 A1 * | 7/2010 | Kamen | A61M 5/14224 604/66 |

FOREIGN PATENT DOCUMENTS

| | | |
|---|---|---|
| WO | 2007/146371 A2 | 12/2007 |
| WO | 2008/052082 A2 | 5/2008 |

* cited by examiner

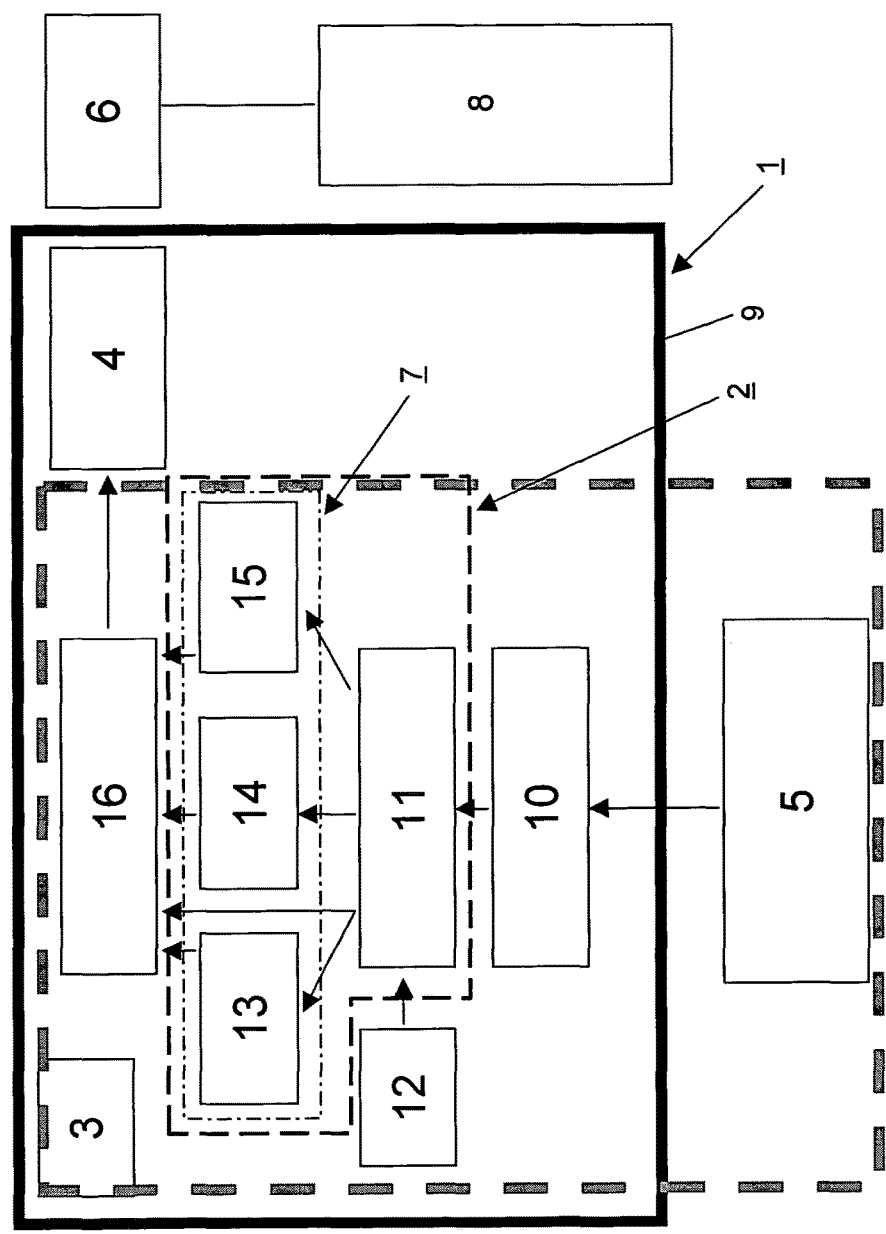

DEVICE FOR PROCESSING AND TRANSMITTING MEASURED SIGNALS FOR MONITORING AND/OR CONTROLLING MEDICAL IMPLANTS, DIAGNOSTIC DEVICES OR BIOLOGICAL PROCESSES

FIELD OF THE INVENTION

The invention relates to a device for processing measured signals which correspond to implant parameters or biological parameters for monitoring and/or controlling medical implants, diagnostic devices or biological processes according to the preamble of claim 1.

Monitoring and controlling of medical implant behaviour has become more and more important. The measurement of implant parameters as strain, displacement, transferred force gives valuable information about the process of bone healing and/or implant distraction. Current wireless techniques allow only short measurements providing restricted information or need to transfer huge amounts of data from the implanted measurement device to an external receiver.

DESCRIPTION OF THE PRIOR ART

A device for providing in vivo diagnostics of loads, wear, and infection in orthopaedic implants is known from U.S. Pat. No. 7,097,662 EVANS. This known device includes a signal processing device which is operable to receive an output signal from at least one sensor and to transmit a signal corresponding with this output signal.

From Graichen F., Rohlmann A., Bergmann G.: "Implantable 9-channel telemetry system for in vivo load measurements with orthopaedic implants", IEEE TRANSACTIONS ON BIOMEDICAL ENGENEERING, Vol. 54, No. 2 February. 2007 another device for in vivo measuring loads to which orthopaedic implants are subjected is known. This known device includes an inductively powered integrated circuit inside the implant which measures six load components as well as the temperature and supplied voltage and a wireless telemetric data transfer system. This known telemetric system requires a power consumption of 5 mW.

The important factors for an implantable data transfer unit are energy consumption and required space. A disadvantage of this known device would be that relatively large lithium button cell (diameter 24 mm×5 mm, 3V) which has a capacity of 540 mAh would have to be implanted. At 5 mW this would mean a theoretical lifetime of this known system of approximatively 13.5 days. Therefore an external power supply via induction is used. Only real-time data can be transmitted since no memory is on board. During the measurements, the patient has to carry a bulky induction coil around his leg plus the RF receiver, since 5 mW only allow a maximum of 0.5 m transmission range.

SUMMARY OF THE INVENTION

It is an object of the invention to provide an electronic device for monitoring of implants which allows to obtain long term measurements of relevant parameters at an implant under minimal energy consumption and minimal required space of the implanted electronic device.

The invention solves the posed problem with a device for processing measured signals which correspond to implant parameters or biological parameters for monitoring medical implants or biological processes that incorporates the features of claim 1.

The advantages achieved by the invention are essentially to be seen in the fact that, thanks to the device according to the invention:
- long term measurements which are most relevant for gaining information about bone healing can be performed by summing up the amplitudes of a cyclic sensor response during physiological loading/unloading and transferring only the sum, the number of cycles and the current sensor value to a wireless receiver outside of the patient;
- a complete assembly including the inventive device and a sensor can be implanted in the patient's body; and
- the data volume can be significantly reduced by providing long term information of the medical implant behaviour at the same time.

The important factors for an implantable data transfer unit are energy consumption and required space. Both are somehow related, the more energy is needed, the bigger the energy carrier has to be. The wireless data transfer is the process requiring the major portion of the energy when using active radio frequency transmission.

By minimizing the amount of data to be transferred, the proposed system guarantees autonomous function for theoretically 9 month, which can also cover healing periods of complicated fractures like mal-unions or critical size defects at an overall size: diameter 30 mm×height 10 mm. Furthermore, the data is believed to be more meaningful since the complete time period is reflected in the values. Particularly relevant statistical data are the sum of the measured signals, the number of measured signals, average value, minimal value and maximal value.

In a special embodiment said signal processing device comprises a programmable electronic data processing unit. The programmable electronic data processing unit can be a programmable microprocessor which allows further data processing and if necessary provides the processed data for a closed control loop e.g. in case of an application of the device as a controller (Measurement of blood sugar and controlling of a device for the deliverance of the medication).

In another embodiment said data transmission device is configured as transreceiver allowing to transmit data and to receive data from an external transmitting source. This configuration allows a transfer of data in both directions, particularly between the device and an external computer.

In a further embodiment said device comprises an electronic data processing unit with an integrator.

In still another embodiment said device further comprises a power supply arranged in said covering. Preferably the power supply is a battery, e.g. a lithium button cell.

In a further embodiment said electronic data processing unit comprises a counter unit allowing to supply the amount of processed signal samples to the data memory. Further, the device can be provided with a timer, an analog/digital converter and signal conditioner.

In yet another embodiment said electronic data processing unit comprises a minimum/maximum unit allowing to identify extreme values in the curve of measured signals. The minmax unit supplies the actual count of cycles in the signal received from the sensor above a predefined threshold to the data memory. This value represents the amount of physiological load cycles or other cyclic processes during a period of time and is a measure for the activity of the patient.

In a further embodiment said data transmission device includes a radio frequency based transmission means. Preferably a radio frequency identification device (RFID) is used, but other devices e.g. known as biotelemetric devices can be used as well. The device sends the information by means of e.g. Radio Frequency Identification (RFID) through the skin. The use of RFID is a further reason for minimizing the data. Here, no internal energy is needed, since the process is fed by induction from outside. Typical data volumes to be transmitted by RFID range between Bytes and 1 kB. RFID is a preferred solution, since required space for the transponder is minimal and the transmission process is fast and simple.

In still another embodiment said device further includes a multi-channel multiplexer. The multiplexer allows to electronically connect a plurality of sensors to the device and to intermittently process the signals received from said sensors.

In a further embodiment the device further comprises at least one sensor. Preferably, the following sensor types are used:
  Displacement, inductivity or other known principles; and/or
  Strain, Strain gauges, particularly wire resistance strain gauges; and/or
  Force, Load cells, strain gage or Piezo based Pressure sensors; and/or
  Acceleration sensors or Temperature sensors; and/or
  Sensors for arterial blood gas parameters (e.g. $CO_2$; $O_2$); and/or
  Sensors for blood sugar; and/or
  Sensors for lactate concentration.
  Particular fields for the use of the device are:
  monitoring of bone healing in osteosynthesis;
  monitoring a bone distraction implant; and
  for providing the processed data in a closed control loop, e.g. monitoring and processing blood sugar values over a certain time period and use of the data for controlling deliverance of the medication.

A BRIEF DESCRIPTION OF THE DRAWINGS

The preferred embodiment of the invention will be described in the following by way of example and with reference to the accompanying drawing in which:

FIG. 1 illustrates a schematic block diagram of an embodiment of the device according to the invention.

The embodiment of the device 1 for processing measured signals illustrated in FIG. 1 comprises a biocompatible sterilizable covering 9 in which an electronic signal processing device 2 allowing to process measured signals received from a sensor 5, a data memory 16 allowing to store data received from said signal processing device 2 and a data transmission device 4 for transmitting data received from said data memory 16 to a remote data receiving device 6 are arranged and electrically connected to each other. Said signal processing device 2 is programmed to calculate statistically relevant data obtained from the said measured signals to reduce the stored data. Particularly, relevant statistical data are the sum of the measured signals, the number of measured signals, average value, minimal value and maximal value. The electronic data processing unit 7 can include an integrator 13, a counter unit 14 allowing to supply the amount of processed signal samples to the data memory 16, a timer 12, an analog/digital signal converter 11 and a signal conditioner 10. Further, the electronic data processing unit 7 is provided with a minmax unit 15 allowing to identify extreme values in the curve of measured signals. The data transmission device 4 is configured as a RFID transponder (Radio Frequency Identification transponder). A power supply 3 is additionally arranged in said covering 9 to operate the device 1 and the sensor 5 (dotted line in FIG. 1) but excluding the data transmission device 4 since the RFID transponder is fed by induction from an external source.

Implantation:

The device 1 comprising the signal processing device 2 and the data transmission device 4 and a power supply 3 in the form of a battery is placed in a biocompatible and sterilizable covering 9 or housing or may be covered by an elastic and biocompatible skin like Latex or Silicon. The sensor 5 is connected via a cable to the device 1. A unit of sensor 5 and the device 1 shall be sterilized prior implantation. In case the sensor 5 can not be mounted to the implant interoperatively (e.g. strain gages) the complete unit of the implant, the device 1 and the sensor 5 have to be preassembled and sterilized together. Another possible solution would be a plug connection between the sensor 5 and the device 1. The complete assembly will then be placed subcutaneously into a pocket of two skin layers.

Internal Data Processing:

The analog signal of the sensor 5 is conditioned by a signal conditioner 10, i.e. a measuring-amplifier and converted to digital data by an 16 bit A/D converter 11 at about 64 Hz sample frequency. All values received from the sensor 5 and further processed by the signal conditioner 10 and the analog/digital converter 11 are digitally summed by an integrator 13 and the sum is stored in the internal data memory 16. Moreover a counter unit 14 is supplying the amount of processed samples (running time) to the data memory 16. A minmax unit 15 identifies extreme values in the curve of measured values and supplies the actual count of cycles in the sensor signal above a predefined threshold to the internal data memory 16. This value represents the amount of physiological load cycles during a time period and is a measure for the activity of the patient. As 4th parameter the actual sensor signal is provided to the data memory 16.

Data Transmission:

The data transmission between the device 1 and an external data processing device 8, e.g. a computer is performed by means of the known technology of Radio Frequency Identification. Four current integer values representing the above described parameters will be provided from the internal data memory 16 to the data transmission device 4, e.g. a RFID transponder and can be transferred to the data receiving device 6, e.g. an RFID receiver at time points to be chosen by the operator. Reasonable data acquisition intervals may range between 1 day and 1 week but depend on the application of the device 1.

The device 1 including the electronic for data acquisition and internal data processing is provided with electrical energy, preferable from a battery like a lithium button cell or comparable. The data transmission device 4 itself is fed by induction based on the RFID principle. With an overall size of the device 1 of: diameter 30 mm×height 10 mm, an autonomous function for theoretically 9 month is possible. The data acquisition frequency is 64 Hz to account for the sampling theorem assuming fast walking or running of the patient. The electronic device 1 is supposed to be implanted subcutaneously and separated to the implant.

Operation of the Device 1:

The assembly including the device 1 and the sensor 5 is in continuous function from the point in time when the power supply 3, i.e. the battery is inserted. This should be when assembling the covering or housing prior sterilization and surgery. The operation of the device 1 ends with removal of the power supply 3, i.e. the battery or loss of electric power, resulting in loss of data in the data memory 16. The current content in the data memory 16 can be read out at any time by means of the data transfer system including the data transmission device 4 and the data receiving device 6.

External Data Processing:

The parameters may be either downloaded and stored on an external data processing device 8, e.g. a computer or directly processed in the data receiving device 6, i.e. the RFID receiver. The sum of sensor response is calibrated to actual units using a linear approach. Subtracting the values of the previous time point from the actual values deliver information about the current period. The sample count divided by the sample frequency provides the running time. The sum of sensor response divided by number of samples gives the mean sensor response of the current period. The sum of sensor response divided by the number of physiological load cycles represents a measure for the sensor response per load cycle.

Meaning of the Results and Presentation:

The mentioned evaluations may be visualized by plotting the measured and processed values over time. For instance, the healing process may be visualized with decreasing average sensor response over time. A threshold can be set for determining the optimal time point for implant removal. For research purposes different dynamization protocols can be evaluated, mal-unions may be identified at an early stage. The progression of the number of physiological load cycles gives information about the patients activity over time and therefore about the stimulation of the bone. For monitoring distraction implants, the current sensor value provides valuable information about the progression of the distraction process.

Application Examples

1. Monitoring of bone healing in osteosynthesis following the principle of secondary healing. The strain in a standard bone plate or intramedullary nail measured by strain gages, could be acquired and processed with the proposed device 1. Reduction of strain could be interpreted as enhanced load sharing of the bone and as progress in the bone consolidation. Knowledge about the healing progression is valuable information to detect mal-unions at an early stage or to determine an optimal time-point for implant removal.

Mechanical stimulation of bone is known to foster bone formation. A tool to monitor dynamization of newly proposed dynamic implants and its progression over time is also an interesting application field for the device 1. It offers the opportunity to acquire long term data rather than repeated short term measurements as done by known techniques.

2. Monitoring of a distraction implant. The method of distracting bone is used for generation of new bone tissue for critical size defects or bone lengthening. The exact telescoping of the implant, like an intramedullary distraction nail is essential to know for optimized bone generation. The inventive device 1 can be used for transmitting the current distraction of the implant as well as the progression of the distraction over time.

3. Measurement of blood sugar and counteraction by controlled release of Insulin. Blood sugar values are monitored and processed over a certain time period and used for controlling deliverance of medication. This can be realized as autonomous control loop inside the body. The values have to be transferred to an external receiver to control the process.

Other application examples are:
Arterial blood gas monitoring ($O_2$, $CO_2$, blood pressure)
Lactate concentrations While various descriptions of the present invention are described above, it should be understood that the various features can be used singly or in any combination thereof. The scope of the present invention is accordingly defined as set forth in the appended claims.

What is claimed is:

1. A device for monitoring healing of a bone after osteosynthesis and for transmitting stored data to a remote receiving device that is connectable to an external data processor, the device comprising:
    at least one sensor configured to measure at least one of strain, displacement and transferred force in the bone or in a bone plate or intramedullary nail implanted into the bone;
    a biocompatible sterilizable covering;
    a signal conditioner arranged in said covering that is electrically connectable to said at least one sensor;
    an electronic signal processing device arranged in said covering comprising
        an analog/digital converter electrically connected to said signal conditioner, and
        an electronic data processing unit electrically connected to said analog/digital converter, said electronic data processing unit comprising an integrator, a counter and a minimum/maximum unit;
    a data memory arranged in said covering and electrically connected to said electronic signal processing device; and
    a data transmission device arranged in said covering and electrically connected to said data memory, said data transmission device being configured to transmit data stored in said data memory to the remote data receiving device;
    wherein the signal conditioner and the analog/digital converter are configured to process measured analog signals of said at least one of strain displacement and transferred force received from the at least one sensor into digital values,
    wherein the integrator is configured to sum the digital values as received from the at least one sensor as processed by the signal conditioner and the analog/digital converter and to provide the sum for storage in said data memory,
    wherein the counter unit is configured to count a number of the processed measured signals and to provide the number for storage in said data memory,
    wherein the minimum/maximum unit is configured to identify minimum and maximum values in a curve of measured signals,
    wherein the electronic signal processing device is configured to calculate statistical data for storage in the data memory, said statistical data including the sum of the measured signals, the number of the measured signals, an average value, and minimal and maximum values,
    wherein the statistical data received by the data memory from the electronic signal processing device for storage has a reduced volume as compared to the measured signals received by the electronic signal processing device from the at least one sensor as processed by the signal conditioner, and
    wherein the data transmission device is an external induction source-fed RFID transponder, which is configured to transfer the statistical data stored in data memory to the remote receiving device.

2. The device according to claim 1, wherein said electronic data processing unit is programmable.

3. The device according to claim 1, wherein said data transmission device is configured as a transceiver for transmitting data to the remote receiving device and for receiving data from an external transmitting source.

4. The device according to claim 1, wherein said device further comprises a power supply arranged in said covering.

5. The device according to claim 1, wherein said device further includes a multi-channel multiplexer.

* * * * *